United States Patent [19]

Baron

[11] Patent Number: 4,761,071
[45] Date of Patent: Aug. 2, 1988

[54] APPARATUS AND METHOD FOR DETERMINING CORNEAL AND SCLERAL TOPOGRAPHY

[76] Inventor: William S. Baron, 330 Willow Rd., Menlo Park, Calif. 94025

[21] Appl. No.: 669,188

[22] Filed: Nov. 6, 1984

[51] Int. Cl.⁴ .............................................. A61B 3/10
[52] U.S. Cl. ...................................... 351/212; 351/247
[58] Field of Search ..................... 351/212, 247, 206

[56] References Cited

U.S. PATENT DOCUMENTS

| | | |
|---|---|---|
| 3,141,396 | 7/1964 | Kimball et al. |
| 3,169,459 | 2/1965 | Friedberg et al. |
| 3,442,579 | 5/1969 | Friedberg |
| 3,486,812 | 12/1969 | Volk |
| 3,519,338 | 7/1970 | Papritz |
| 3,536,384 | 10/1970 | Cocks |
| 3,842,254 | 10/1974 | Dianetti ............................ 351/212 X |
| 4,019,813 | 4/1977 | Cornsweet et al. |
| 4,159,867 | 7/1979 | Achatz et al. |
| 4,315,672 | 2/1982 | Müller et al. ............................ 351/212 |
| 4,355,871 | 10/1982 | Nevyas et al. |
| 4,420,228 | 12/1983 | Humphrey |
| 4,429,960 | 2/1984 | Mocilac et al. |
| 4,533,223 | 8/1985 | Duparchy ............................ 351/206 |
| 4,540,254 | 9/1985 | Humphrey ............................ 351/212 |
| 4,572,628 | 2/1986 | Nohda ............................ 351/212 |

OTHER PUBLICATIONS

Kawara, "Corneal Topography Using Moire Contour Fringes," 18 Applied Optics, 3675–78 (1979).
Fujii et al., "Determination of Corneal Configuration by the Measurement of its Derivatives," 19 Optica Acta, 425–30 (1972).

Primary Examiner—Rodney B. Bovernick

[57] ABSTRACT

An apparatus and method for determining the topography of the cornea and sclera that permit the detailed determination of the topography of the entire visible corneal and scleral surfaces; the topographic data so obtained is readily and conveniently accessible to the opthalmic practitioner or surgeon. A fluorescent substance instilled in the tear layer of the eye, and hence the surface of an eye, is made to fluoresce in a small, selected area of the eye surface by an incident light beam defining the selected area of the eye surface. The location of the selected area can be known from the position and direction of the incident light beam. The selected area's location is measured from at least one additional orientation different from that of the incident light beam by focusing an image of the fluorescence emissions from the selected area onto the surface of a positive sensitive detector. The elevation of the eye surface in the selected area is determined by triangulation or profiling, depending on the direction of the fluorescence detection. A plurality of such measurements made at different locations on the surface of the eye permits the topography of the corneal and scleral surfaces of the eye to be determined.

60 Claims, 4 Drawing Sheets

APPARATUS AND METHOD FOR DETERMINING CORNEAL AND SCLERAL TOPOGRAPHY

BACKGROUND OF THE INVENTION

1. Field of the Invention

This invention relates to an apparatus and method for determining the surface topography of the cornea and sclera of an eye.

2. Brief Description of the Prior Art

Methods and instruments for determining the surface curvature of the cornea by keratometry are known. Keratometers utilize a variety of optical systems to observe the size and shape of the image of a target mire as reflected and refracted from the eye. Information regarding the surface symmetry and curvature of the cornea in a relatively small area near the center of the cornea may be deduced using keratometers, such as recently disclosed in U.S. Pat. Nos. 4,420,228 or 4,429,960. However, because all keratometry involves the approximation of the corneal surface as one or another relatively high symmetry conic surface, such as a spherical or ellipsoidal surface, information obtained by keratometry about the actual corneal topography is limited. The problem is acute when attempting to examine pathological and post-surgical corneas. The information obtained by keratometry is often insufficiently detailed for the proper fitting of contact lenses, or for the demands of eye surgery. The utility of keratometry is further limited in that it can be used to measure eye surface curvature only in the center of the cornea and not in the periphery of the cornea, in the transition area between the cornea and the sclera (the limbus), or on the sclera itself.

Several techniques have been proposed for measuring the topography of the corneal surface. These include stereophotography of a light pattern projected onto the eye and analysis of the stereophotographs photogrammetrically (Friedberg, et al., U.S. Pat. No. 3,169,459). Derivatives of the surface curvature have been measured both manually (Volk, U.S. Pat. No. 3,486,812) and by photography of reflected light through a telecentric optical system, followed by integration of the data to determine the topography (Fujii, et al., 19 Optica Acta 425 (1972)). Kawara, 18 Applied Optics 3675 (1979), discloses a method of determining topography by photographing moiré contour fringes derived from a projected fluorescence pattern. Determination of the corneal profile has been accomplished by illumination of the eye with a slit lamp in combination with recording by photography (Kimball, et al., U.S. Pat. Nos. 3,141,396 and Papritz, 3,519,338) or a vidicon camera (Cornsweet, et al., U.S. Pat. No. 4,019,813). The phase shifts of the reflections of sonic compressional waves have also been measured to determine eye topography (Friedberg, U.S. Pat. No. 3,442,579). None of these approaches to topography determination has found wide clinical acceptance due to excessive cost, lack of accuracy or inconvenience of use. Some of these techniques are restricted to measurements of just the corneal surface. Photographic procedures involve two distinct steps; after the photographs are taken, they must be separately analyzed. Further, such procedures are prone to calibration and measurement errors due to film dynamics and uncertainties in the measurements of indistinct images. Such procedures are also time consuming and inconvenient in the clinical setting. Computer analysis of vidicon pictures tends to be expensive and is often inaccurate due to signal extraction problems.

SUMMARY OF THE INVENTION

The present invention provides an apparatus and method for determining the topography of the cornea and sclera. The invention permits the detailed determination of the topography of the entire corneal and scleral surfaces; the topographic data so obtained is readily and conveniently accessible to the ophthalmic practitioner or surgeon. Briefly, a fluorescent substance instilled in the tear layer of an eye is made to fluoresce in a small, selected area of the eye surface by an incident light beam defining the selected area of the eye surface. The location of the selected area can be known from the position and direction of the incident light beam. The selected area's location is measured from at least one additional orientation different from that of the incident light beam by focusing an image of the fluorescence emissions from the selected area onto the surface of a position sensitive detector. The elevation of the eye surface in the selected area is determined by either triangulation or image profiling, depending on the direction of the fluorescence detection. A plurality of such measurements made at different locations on the surface of the eye permits the topography of the corneal and scleral surfaces of the eye to be determined.

Generally, the apparatus according to this invention comprises a first optical branch for generating the incident light beam, a second optical branch for measuring the location of the fluorescence emissions from the selected area, and system electronics, including a digital computer for gathering and analyzing the topographic information. The first optical branch includes a light source and optical elements for collecting and directing light emitted by the light source along a first optical axis toward a small area of the eye surface. Deflection optics included in the first optical branch are provided to vary the displacement of this incident light beam so that the area of the eye surface on which it impinges may be selected. The extent and direction of deflection of the incident light beam, and thus the position of the selected area, may be determined electronically.

The second optical branch includes a photoelectric transducer made approximately conjugate with the eye surface by suitable focusing optics. The position of the selected area, as viewed from the perspective of the second optical branch, is determined by detecting the focused fluorescence emissions arising from the surface of the eye in the selected area. The photoelectric transducer is sensitive to the position of the focused fluorescence emissions and produces electronic signals representative of this position. These electronic signals are converted into a form appropriate for computer input.

Because the computations required for the analysis of the data obtained are relatively simple, the topographic information derived from the data is conveniently and rapidly available to the practitioner even when utilizing a computer of only modest capacity. Additionally, the detection of emissions of a fluorescent substance "marker" on the eye surface eliminates many of the difficulties inherent in photographic or video imaging processes which use a machine to differentiate the desired image from a noisy background.

In the preferred embodiment, the incident light beam is filtered to include only wavelengths shorter than the fluorescence emission wavelengths, and the second optical branch is provided with a cut-off filter to remove any incident light beam wavelengths. These filters assure that only light emitted from the surface of the eye is detected by the second optical branch. Modulation of the incident light beam, and thus of the fluorescence emissions, and synchronous measurement of the electronic signals produced by the second optical branch serve to minimize interference by stray light from external sources, such as ambient light.

The system electronics preferably include conventional components for synchronous measurement of the electronic signals derived from the photoelectric transducer and deflection sensor, and for conversion of the signals from analog to digital form, and a digital computer for collection and analysis of the data.

In a second embodiment of the invention, a portion of the incident light beam is diverted before the incident light beam reaches the beam deflector and is directed along another path to the eye surface. A second area of the eye surface is thus illuminated and caused to fluoresce. However, one of these areas is undeflected and thus serves as a reference "spot" to enable corrections for possible eye movements during the process of collecting sufficient data to determine the topography of the eye surface. This reference position can be used either to correct the positioning of the first optical axis with respect to the eye, or to apply corrections to the data accumulated by the computer.

This invention, by determining the topography of the eye surface, is thus not limited to parameterizing an assumed curvature of the corneal surface, but allows the corneal surface to be determined in detail. Since instruments utilizing this invention detect only fluorescence diffusely emitted at the surface of the eye, errors due to reflection and refraction of light by the structures of the eye are largely eliminated. The invention allows the determination of the topography of the entire corneal and adjacent scleral surfaces, since it does not rely either on an assumed, high symmetry eye surface or on the reflective character of the eye surface. Also, since the topographic information may be rapidly and conveniently accumulated and analyzed by a digital computer, the topography determined is made readily and conveniently accessible to ophthalmic practitioners. Other advantages and adaptations of the invention will be apparent to those skilled in the art.

DETAILED DESCRIPTION OF THE PREFERRED EMBODIMENTS

Figure 1:
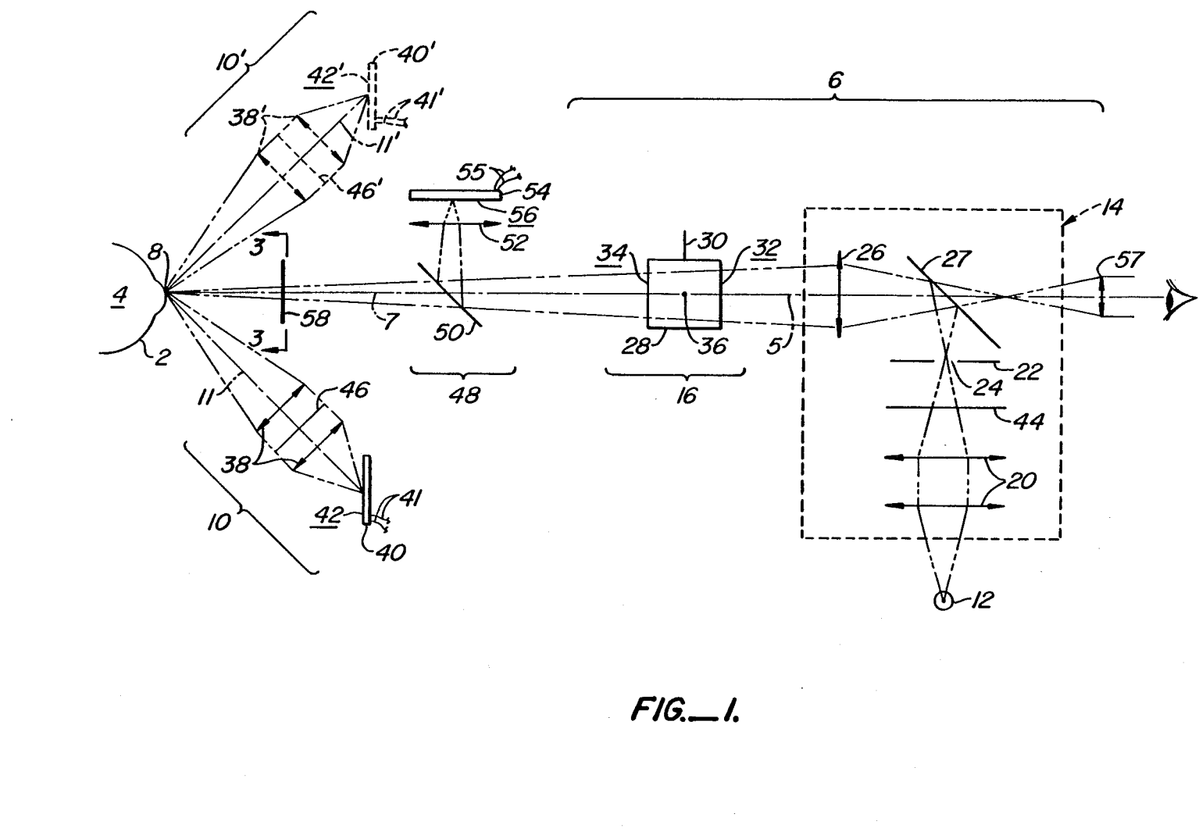
FIG. 1 is a schematic view of the preferred embodiment of the invention.

FIG. 1 is a schematic view of the preferred embodiment of the invention. FIG. 1 also schematically shows an eye 4, whose tear layer and hence surface 2 is infused with a fluorescent substance. In its broadest terms, this embodiment of the invention includes a first optical branch 6 for producing an incident light beam 7 impinging on a selected area 8 of surface 2 of eye 4, thereby causing the fluorescent substance in the selected area to emit light, and a second optical branch 10 for detecting the light emitted by the fluorescent substance in the selected area. From knowledge of the position and incidence direction of the incident beam at selected area 8 and the position of selected area 8 determined with second optical branch 10, the elevation of selected area 8 of eye surface 2 may be determined by either triangulation or by image profiling. From measurements of the elevation of eye surface 2 at a plurality of locations on the eye surface, the topography of the eye surface may be determined.

In this specification and the appended claims, references will be made, for example, to light "directed to" a point or optical element, such as a lens or mirror. References will also be made to a "propagation direction" of light. Since the light referred to frequently encompasses a plurality of light rays with individually different directions generally converging on or diverging from a particular location, "light direction" or "propagation direction" will be understood to refer to the direction of the centroid of the light beam, or its "chief ray." As used in this specification, two points, surfaces, or structures are "conjugate" if a luminous point located at either of the two points, surfaces, or structures is imaged at the other of the two points, surfaces, or structures. In addition, in this specification and the appended claims, the terms "infuse" and "instill" are used synonymously.

First optical path 6 includes a light source 12, a director 14, and a deflector 16. In the preferred embodiment, director 14 collects a portion of the light emitted by light source 12 and directs it toward deflector 16 along a first optical axis 5. Deflector 16 is operable to deflect the light emergent along first optical axis 5 from director 14 to different locations on eye surface 2, thereby varying the selected area.

In the preferred embodiment, light source 12 is a stroboscopically operable gas-filled discharge lamp. The operation of light source 12 is controlled by an associated power supply (not shown). In alternate embodiments, light source 12 may be one of a variety of light emission devices, for example, an incandescent lamp, a low power laser, or a light emitting diode.

Director 14 preferably includes a first focusing element 20, an opaque aperture plate 22 defining a transparent aperture 24, a second focusing element 26, and a partial reflector 27. First focusing element 20 collects light emitted by light source 12 and directs it to aperture 24 defined in aperture plate 22. First focusing element 20 is chosen so that light source 12 and aperture 24 are approximately conjugate. Light passing through aperture 24 is directed towards eye surface 2 along first optical axis 5 by second focusing element 26. Aperture 24 and eye surface 2 are made approximately conjugate by second focusing element 26. Although second focusing element 26 is indicated in FIG. 1 as a single convex lens, it may prove convenient for second focusing element 26 to include a combination of lenses.

Partial reflector 27 is provided to reflect light emergent from aperture 24 at about a right angle to second focusing element 26. Partial reflector 27 transmits at least part of any light impinging upon it from the direction of eye 4. Partial reflector 27 is preferably a partially silvered mirror, although suitable substitutes will be apparent to those skilled in the art. Partial reflector 27 enables the operator to view the eye surface 2 through a telescopic eyepiece 57 to aid in properly orienting first optical branch 6 with respect to eye 4, as discussed below. In alternate embodiments of this invention, light source 12, first focusing element 20, aperture 24, and second focusing element 26 may be approximately collinear, in which case partial reflector 27 is omitted. Similarly, in an alternate embodiment utilizing a point light source 12 positioned adjacent to aperture 24, first focusing element 20 could be omitted.

Director 14 thus generally serves to gather light from light source 12 and focus it at a point in a plane near eye surface 2. In the preferred embodiment, incident beam 7 is focused by second focusing element 26 so that selected area 8 has a diameter of approximately one millimeter.

Deflector 16 is provided to vary the position of selected area 8 on eye surface 2. While several such devices will be apparent to those skilled in the art, the preferred embodiment utilizes an optical cube 28 that is rotatable about an axis 30 that is generally orthogonal to the direction of first optical axis 5. Optical cube 28 has parallel opposing surfaces 32 and 34, and is preferably made of optically transparent plastic, although other optically transparent materials would suffice. As optical cube 28 is rotated about axis 30, the light impinging upon surface 32 is refracted at surfaces 32 and 34 so that the light emerges from surface 34 parallel to, but displaced from, first optical axis 5. When optical cube 28 is rotated, the selected area 8 of eye surface 2 is varied (or "scanned") along a meridian of the eye surface 2. The use of optical cube 28 for deflector 16 is convenient since incident beam 7 is translated relative to first optical axis 5 when optical cube 28 is rotated. Other optical elements having parallel surfaces could be utilized to achieve a similar deflection pattern. However, this deflection pattern is not necessary to the invention. Deflector 16 could comprise a rotating or oscillating mirror; such an embodiment would vary the angular displacement of the incident light beam to vary the position of selected area 8 on eye surface 2. Other means for varying the selected area 8, such as mechanically coupled prisms, will be apparent to those skilled in the art. In such alternate embodiments, it may be necessary to alter director 14 so that light is emergent from director 14 in a direction different from that indicated as first optical axis 5, as will be apparent to those skilled in the art.

To vary the meridian of the surface of the eye over which the light is directed, and hence increase the part of eye surface 2 for which the topography can be determined, the entire first optical branch 6 could be rotated about the direction of first optical axis 5, thereby varying the inclination of the meridian of eye surface 2 scanned by rotating optical cube 28. However, it is convenient to provide other means for accomplishing this task. Mechanisms for accomplishing the required rotations are well known in the art. Alternatively, a second rotatable optical cube (not shown), disposed between optical cube 28 and eye 4, could be rotated about a second axis to deflect the incident light beam 7 to any location on the surface of the eye. A dove prism rotatable about an axis parallel to first optical axis 5 could also be used to vary the meridian of eye surface 2 scanned by incident light beam 7.

Rotatable optical cube 28 is preferably rotated by a motor (not shown); this is an electric motor of a conventional type. A stepping motor could be used to rotate optical cube 28 in alternate embodiments.

The fluorescent substance is instilled in the tear layer and hence on eye surface 2 in a manner well known to those skilled in the art, as, for example, by dropwise addition of an aqueous solution of sodium fluorescein to the palpebral aperture of the eye 4. Other fluorescent substances or mixtures of substances suitable for infusion on the surface of the eye will be apparent to those skilled in the art. The light emitted from source 12, directed towards the eye by director 14 and varied in position by deflector 16 causes the eye surface 2 to fluoresce in the selected area 8. The use of a fluorescent substance on the surface 2 of the eye 4 allows the detection primarily of light whose source is the eye surface 2, rather than the detection of multiply-reflected and/or refracted images of incident light beam 7. In addition, the fluorescence is emitted from the selected area 8 in all directions and can thus be measured from any orientation which is convenient for the topography determination.

Second optical branch 10 includes an imager 38 and a photoelectric transducer 40. Second optical branch 10 defines second optical axis 11, separated from first optical axis 5 at a known angle, as discussed below. The point at which second optical axis 11 intersects eye surface 2 is not critical. Second optical branch 10 lies along a second optical axis 11 from eye surface 2 such that the surface 42 of photoelectric transducer 40 is made approximately conjugate with selected area 8 by imager 38. Photoelectric transducer 40 is sensitive to the position of the image of selected area 8 formed by imager 38 on surface 42 of photoelectric transducer 40, and produces electrical signals through position leads 41 that are proportional to the image's position. Since the electrical responses produced by photoelectric transducer 40 are indicative of the centroid of light impinging on its surface, the eye surface 2 and transducer surface 42 need only be approximately conjugate. For this reason, although the distance between selected area 8 and the point on transducer surface 42 at which the image is formed varies as selected area 8 is varied over eye surface 2, this variation does not affect the accuracy of the data obtained, and second optical branch 10 need not be refocused as selected area 8 is varied on eye surface 2. A variety of photoelectric transducers 40 will be known to those skilled in the art; the preferred transducer 40 is a continuous position sensitive silicon detector. However, a diode matrix, linear diode array, vidicon or other position sensitive detector could be adapted for use in alternate embodiments.

In the preferred embodiment, the first optical axis 5 and the second optical axis 11 are mutually oriented at an angle of between about 20° and about 70° and preferably about 30°. The actual angle is not crucial and is chosen to minimize errors in the determination of the position of selected area 8. The orientation of second optical branch 10 relative to axis 30 about which optical cube 28 is rotated is not critical, but there are two preferred orientations. In the first, second optical axis 11 lies in the plane defined by the scan of incident light beam 7. In the other preferred orientation, the plane defined by first and second optical axes 5 and 11 is perpendicular to the scan plane of incident light beam 7. These two orientations correspond to the rotation of optical cube 28 about the axes indicated in FIG. 1 as 36 and 30, respectively. The orientation of second optical axis 11 relative to the scan plane of incident light beam 7 also determines the requirements of photoelectric transducer 40. When second optical axis 11 is in the scan plane, photoelectric transducer 40 may be a device that is sensitive to the position of an illuminated area of transducer surface 42 along a single direction in the plane defined by the scan plane. With other second optical axis 11 orientations, photoelectric transducer 40 is a dual axis device, as discussed above. A single axis photoelectric transducer 40 is preferred for minimizing transducer response time and maximizing sensitivity. A single axis transducer also reduces the complexity of the supporting electronics, as will be apparent to one skilled in the art.

When second optical axis 11 is located in the scan plane, the topographic information is derived by triangulation. For each selected area 8 along a meridian of the eye, defined by the intersection of the scan plane and the eye surface 2, the elevation of selected area 8 is determined by simultaneously solving two equations, each containing two unknowns. The equations represent lines defined respectively by the incident light beam 7 and a line from selected area 8 to the nodal point of imager 38, which is known from the natures and positions of the components of second optical axis 10. Each equation is of the general form $$ax + by = c \qquad \text{eq. (1)}$$

where the constants are determined from the geometry of the apparatus or measured by photoelectric transducer 40.

Figure 2A:
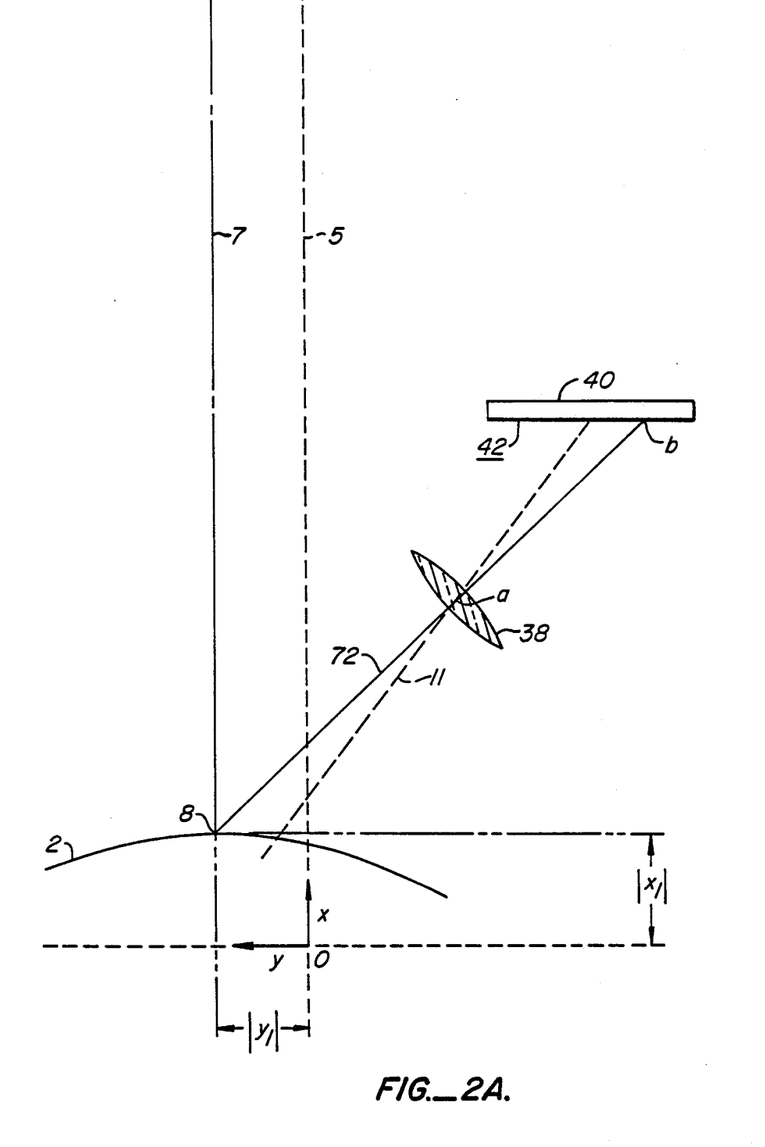
FIG. 2A is a diagram illustrating a simplified example of the calculation of the elevation of a selected area of the surface of the eye.

As an example for illustrative purposes only, FIG. 2A shows the set-up of a simplified calculation of the elevation of selected area 8. The calculation of the elevation of selected area 8 is performed by determining the point of intersection of the incident light beam 7 and the chief ray of the fluorescence emission 72 from selected area 8. Incident light beam 7, first optical axis 5, and second optical axis 11 are all taken to lie in the same plane. This plane is taken to be the x-y plane with the x-axis parallel to incident light beam 7. The incident light beam 7 is displaced from the x-axis by some amount $y_1$, and can be represented by a simplified form of equation (1):

$$y = y_1 \qquad \text{eq. (2)}$$

Assuming for the purposes of this illustration that imager 38 is a thin lens, the chief fluorescence ray 72 passes through the nodal point of imager 38 to a point on photoelectric transducer surface 42. The center of imager 38 (point a) and the point on surface 42 (point b) are also located in the x-y plane and have coordinates $(x_a, y_a)$ and $(x_b, y_b)$, respectively. Each of these coordinates is known from the geometry of the apparatus or measured with photoelectric transducer 40. Chief ray 72 can now be described by the equation:

$$\frac{y - y_a}{y_b - y_a} = \frac{x - x_a}{x_b - x_a} \qquad \text{eq. (3)}$$

Selected area 8 lies at the intersection of the lines of incident light beam 7 and the chief ray 72, and thus has coordinates $(x_1, y_1)$, which are determined by solving equations (2) and (3) to yield values for $x_l$ and $y_l$. Since $y_1$ was defined by the displacement of the incident light beam 7 in this example, $$x_1 = \frac{(x_b - x_a)(y_1 - y_a)}{(y_b - y_a)} + x_a \qquad \text{eq. (4)}$$

The elevation of selected area 8 is $x_l$. The calculation is analogous if imager 38 is a thick lens or combination of lenses; the necessary calculations will be known to those skilled in the art. The calculations are more complex if incident light beam 7 is not parallel to the x-axis, and eq. (2) will be of the form of eq. (1). The elevation of each selected area 8 together describe the topography of the meridian scanned.

If the second optical axis 11 is outside the scan plane, photoelectric transducer 40 must be a dual axis device. The topographic information for an entire meridian can be deduced either by triangulation or from the information derived from transducer 40 and the angle between first and second optical axes 5 and 11. In the case of triangulation, the calculation is analogous to the above calculation except that the equations describing incident light beam 7 and chief ray 72 each contain three unknowns, since three coordinates are required to describe the position of a point. Since incident light beam 7 and chief ray 72 are required to intersect at selected area 8, these equations can be solved to yield the position of selected area 8.

Figure 2B:
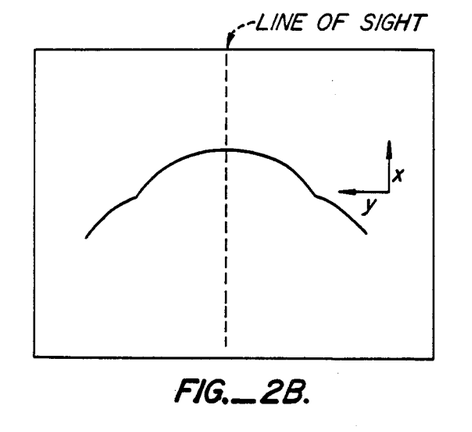
FIG. 2B is a diagram representing the output of the photoelectric transducer for an embodiment in which the second optical axis is outside the scan plane.

Alternatively, when second optical axis 11 is outside the scan plane, since a scan is restricted to a single meridian, the profile of the eye is represented directly by the output of transducer 40. A representative output is shown schematically in FIG. 2B. In FIG. 2B the position-outputs of transducer 40 are shown in a cartesian coordinate frame; the line of sight axis is shown as a reference. This data need be corrected only for the angle of second optical axis 11 with respect to first optical axis 5 in order to represent the topography of the meridian scanned. This correction can be made either mathematically or by orienting transducer surface 42 in a plane orthogonal to first optical axis 5.

The above discussion applies to the analysis of a single meridian of the eye. To characterize the entire surface of the eye, the meridian scanned is varied, as discussed above.

In an alternate embodiment of the invention, a third optical branch 10' is utilized to determine replicate measurements of the position of selected area 8. Third optical path 10' is indicated in ghost outline in FIG. 1. The components of third optical branch 10' are each typically equivalent to the analogous portions of second optical branch 10 and are numbered accordingly in FIG. 1.

In this alternate embodiment, second optical axis 11 and third optical axis 11' are oriented at about 60° apart and may be coplanar with first optical axis 5. The use of second and third optical branches 10 and 10' enables the selected area 8 to be determined from two directions, thereby increasing the accuracy with which the elevation of selected area 8 of eye surface 2 may be deduced. In addition, this embodiment reduces possible systematic errors in the triangulation of selected area 8, which may be caused by fluorescence emissions from areas of eye surface 2 outside selected area 8. Such extraneous emissions arising from reflection and/or refraction of incident light beam 7 internally of eye 4 will cancel by averaging the triangulation measurements from two directions 11 and 11' equally spaced apart from the first optical axis 5.

Since photoelectric transducer 40 is typically responsive to wavelengths of light other than those emitted by the fluorescent substance, photoelectric transducer 40 will be responsive to light from incident beam 7 reflected or refracted by eye 4 onto detector surface 42. To avoid the resulting errors in measurement of the position of selected area 8, first and second optical branches 6 and 10 of the preferred embodiment include optical filters 44 and 46, respectively. Filter 44 is chosen so that it is substantially transparent to light having wavelengths shorter than those of the light emitted by the fluorescent substance instilled in the tear layer of the eye, and substantially opaque to light having wavelengths equal to the fluorescence emission of the fluorescent substance. In the preferred embodiment, using sodium fluorescein as the fluorescent substance instilled in the eye, filter 44 is substantially transparent to wavelengths shorter than about 500 nanometers and substantially opaque to longer wavelengths. Filter 46 is chosen so that it is substantially transparent to the fluorescence emissions of the fluorescent substance instilled on the surface of the eye, and substantially opaque to the light transmitted by filter 44. The locations of optical filters 44 and 46 within the first optical branch 6 and second optical branch 10, respectively, are not critical, but are consistent with their intended function.

In an alternate embodiment, director 14 is simplified if light source 12 comprises a low-power laser, such as a semiconductor diode laser. If a laser is used for light source 12, first and second focusing elements 20 and 26, aperture plate 22, and optical filter 44 are unnecessary. Instead, the laser output of a wavelength capable of exciting the fluorescent substance would be directed toward deflector 16 and eye 4. In this alternate embodiment, second optical branch 10 will be as described above to determine the location of the selected area and prevent responses of photoelectric transducer 40 to light from incident beam 7 that has been scattered from eye 4.

In the preferred embodiment, an excitation locator 48 is used to measure the extent of deflection of incident beam 7 caused by deflector 16. Excitation locator 48 comprises a beam splitter 50, a lens 52, and an incident beam detector 54. Beam splitter 50 reflects a portion of incident light beam 7 through lens 52 to incident beam detector 54 without altering the direction of incident light beam 7. Lens 52 focuses the reflected portion of incident light beam 7 onto the surface 56 of incident beam detector 54. The surface 56 of incident beam detector 54 is thus made approximately conjugate with aperture 24 by lens 52, second focusing element 26, and beam splitter 50. Incident beam detector 54 preferably comprises a continuous position sensitive silicon detector. Other sensing devices that may suitably be substituted for incident beam detector 54 will be apparent to those skilled in the art. For example, a diode matrix adapted to produce electrical signals proportional to the position of the portion of incident light beam 7 reflected onto detector surface 56 could be used. Similarly, a vidicon or linear photodiode array could be used. The electrical signals produced by incident beam detector 54 at location leads 55 are proportional to the direction of incident light beam 7 with respect to eye 4 and the extent of deflection of the incident beam by deflector 16.

Preferably, optical cube 28 is associated with a disk (not shown) that is alternately opaque and transparent at regular intervals around its periphery and mounted to rotate synchronously with optical cube 28 about axis 30 or 36. A light emitting diode (LED) and an optically activated microswitch are positioned on either side of the periphery of the disk, so that when a transparent interval passes between the LED and the microswitch, the microswitch produces an electrical pulse. The extent of rotation of optical cube 28 may then be measured by counting the pulses so produced, in a manner well known in the art. In alternate embodiments of the present invention, the degree of rotation of optical cube 28 about axes 30 and/or 36 may be measured electronically by potentiometric sensors coupled to optical cube 28 and sensitive to the extent of rotation of optical cube 28. Suitable sensing means (not shown) for potentiometrically measuring the degree of rotation of optical cube 28, or for measuring the extent of beam deflection for other deflectors 16, will be apparent to those skilled in the art. The position information derived from either excitation locator 48 or electronic rotation measurements is used to triangulate the elevation of the eye surface 2 in the region of the selected area 8, as discussed above.

Figure 3:
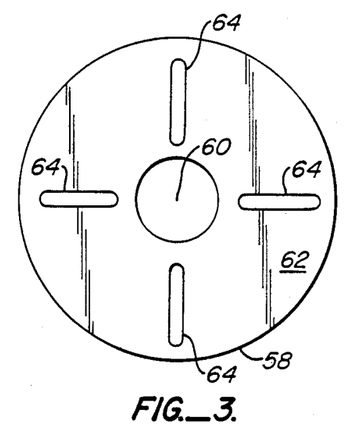
FIG. 3 is a partial section view showing the mire from the direction of the eye.

The alignment of first optical branch 6 is guided by a telescopic eyepiece 57 in conjunction with a mire 58. The preferred mire 58 is shown in greater detail from the perspective of eye 4 in FIG. 3. Mire 58 is an opaque disc oriented normal to first optical axis 5 and has a hole 60 through which the incident light beam 7 passes. Mire 58 is disposed between incident beam locator 48 and eye 4. The surface 62 of mire 58 adjacent eye 4 has self-luminous or diffusely-reflective areas 64 arranged in a target pattern, such as the ends of a cross. Other suitable target patterns and mires will be apparent to those skilled in the art. With optical cube 28 in an orientation in which the incident light beam 7 is undeflected from first optical axis 5, an image of the self-luminous areas 64 reflected from the eye is viewed through telescopic eyepiece 57 to aid in orienting first optical axis 5 with respect to eye 4, preferably along the line of sight axis. Preferably, a reticule (not shown) is provided in eyepiece 57 to provide the operator with a guide for alignment. A fixation point for the patient near first optical axis 5 between the eye and deflector 16 may also be provided in a manner well known in the art. Deviations of first optical axis 5 from the line of sight axis are permissible, as long as the extent and angle of deviation of the two directions are known.

The intensity of the light emitted by light source 12 is preferably modulated by means well known in the art and adapted to the particular light source 12 used. In the preferred embodiment, light source 12, a stroboscopically operable gas filled discharge lap, is modulated by the regulation of the discharge lamp power supply (not shown). In alternate embodiments, light source 12 may be modulated with a Kerr-cell shutter or with a light chopper, which periodically interposes an opaque barrier between light source 12 and director 14. Mechanisms suitable for light choppers and arrangements for Kerr-cell shutters are well known in the art. The modulation rate is preferably in the range of about 10 Hz to about 50 kHz. Modulation of the light emitted from the light source 12 and synchronous detection of the electronic signals produced by photoelectric transducer 40 and incident beam detector 54 are advantageous for several reasons. First, the electronic signals can be measured with enhanced sensitivity and accuracy. Second, the responses of photoelectric transducer 40 to the fluorescence emission from selected area 8 and the responses of incident beam detector 54 to the reflected portion of incident light beam 7 are readily differentiated from noise due to stray light, such as room light.

Figure 4:
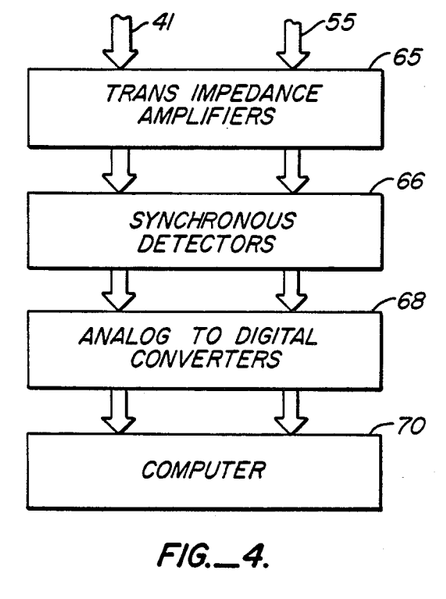
FIG. 4 is a block diagram of the system electronics of the preferred embodiment.

The desired electrical signals produced by photoelectric transducer 40 at position leads 41 and by incident beam detector 54 at location leads 55 are thus also modulated and may be synchronously measured. FIG. 4 shows, in block diagram form, the components of the electronics used to determine the topography of eye surface 2. Each of the individual components shown in FIG. 4 is of a conventional type, well known in the art. Position leads 41 and location leads 55 are each connected to transimpedance amplifiers 65 and then to synchronous detectors 66. In the preferred embodiment, synchronous detectors 66 are gated integrators; alternate methods of synchronous detection, such as lock-in amplifier or sample-and-hold circuits could be used in alternate embodiments. The outputs of synchronous detectors 66 are preferably converted to digitally encoded voltages by analog-to-digital converters 68. The digitally encoded voltages are then input into digital computer 70 for calculation of the surface topography of the eye by methods known to those skilled in the art. The topographic information can be displayed or otherwise rendered accessible to the operator by a suitable means (not shown). Although each lead 41 and 55 could have an associated analog-to-digital converter, the outputs of synchronous detectors 66 could be input into a multiplexer (not shown) and processed serially by a single analog-to-digital converter 68. Alternatively, the digitally encoded voltages from the analog-to-digital converters 68 could be similarly multiplexed for serial input to computer 70.

Figure 5:
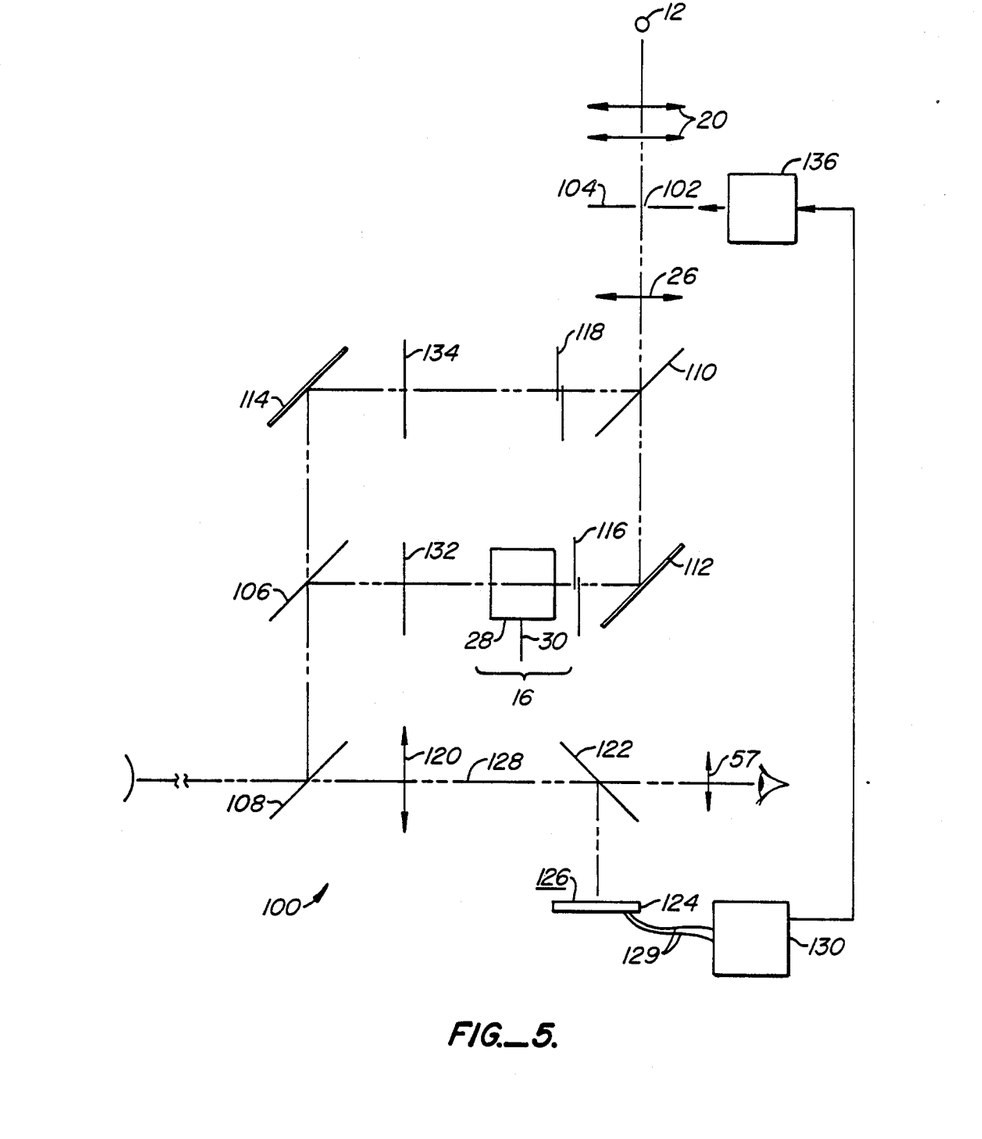
FIG. 5 is a schematic view of the first optical branch of a second embodiment of the invention.

FIG. 5 is a schematic of a second embodiment of the invention. As with the first embodiment, this embodiment has first and second optical branches; the first optical branch 100 is shown; the remaining components of the second embodiment being as described above for the preferred embodiment. Several of the components of first optical branch 100 are equivalent to those of the preferred embodiment. These will be numbered as in FIG. 1; the discussion of the characteristics and operation of equivalent components will be largely omitted below.

In the second embodiment, light emitted by light source 12 is collected and focused through an aperture 102 defined in an aperture plate 104 by first focusing element 20. Aperture plate 104 is made electromechanically translatable in each of two orthogonal directions, each orthogonal to the direction of the light, by an aperture controller 136, such as a servo mechanism. Aperture 102 is made approximately conjugate with eye surface 2, although the light is reflected from first mirror 112 and second and third beam splitters 106 and 108 before it reaches eye surface 2. First beam splitter 110, which may be, for example, an approximately 50% silvered mirror, divides the light into a reference beam and a sampling beam. The reference beam is reflected by first beam splitter 110, second mirror 114 and third beam splitter 108 to eye surface 2. The sampling beam is transmitted through deflector 16, preferably an optical cube 28 rotatable about axis 30, as discussed above in connection with the preferred embodiment. The sampling beam is then directed to eye surface 2 by second and third beam splitters 106 and 108. Mirrors 112 and 114 and beam splitters 106, 108, and 110 are arranged such that, when the sampling beam is undeflected by deflector 16, the sampling and reference beams are coincident at eye surface 2. The reference and sample beams are filtered by optical filters 134 and 132. Optical filter 132 is equivalent to first optical filter 44, discussed above. Optical filter 134 can pass wavelengths in addition to those passed by optical filters 132 or 46. The sampling beam is deflected to different selected areas 8 on the eye surface 2 by deflector 16, as discussed above. The extent of deflection is measured by excitation locator 48, also as discussed above in connection with the preferred embodiment. The reference beam is undeflected and causes eye surface 2 to fluoresce at the same reference spot (not separately shown) as long as the eye is not moved during the topography measurement procedure. If the eye does move, as when the patient momentarily shifts his eye, the reference spot can be used to (1) correct the data obtained and (2) compensate for eye movement by changing the position of both the reference and sampling beams, as discussed below.

The reference and sampling beams are modulated in intensity at first and second modulation frequencies by reference and sample modulators 118 and 116, respectively. The use of different frequencies to modulate the reference and sample beams enables the separate and simultaneous measurement of the positions of the images of selected area 8 and the reference spot (not shown) on the surface 42 of photoelectric transducer 40. This is accomplished, as will be apparent to those skilled in the art, by synchronously measuring the signals produced by photoelectric transducer 40 at each of the first and second modulation frequencies.

Additionally, monitoring of the location of the reference spot's fluorescence emission with second optical branch 10 provides sufficient information to correct for eye movements parallel to first optical axis 128 and for other eye movements during the measurement period since selected area 8 is moved relative to the reference spot (not separately shown).

In the second embodiment, reflections of the reference beam from eye 4 can be monitored for eye movement with a lens 120, a fourth beam splitter 122 and a reference detector 124. The surface 126 of reference detector 124 and eye surface 2 are made approximately conjugate by lens 120 and fourth beam splitter 122. Preferably, lens 120 is chosen so that the image of the reflection formed on reference detector surface 126 is slightly defocused. Reference detector 124 is preferably a quadrant position sensitive silicon detector, capable of detecting deviations of an illuminated area away from the center of the detector surface into any of four quadrants. A continuous position sensitive silicon detector, diode matrix, or vidicon could be used for reference detector 124. Reference detector 124, fourth beam splitter 122, and lens 120 are preferably, aligned such that, when the reference spot is located on the corneal apex of eye surface 2, the image of the reference spot is centered on reference detector surface 126. Beam splitter 122 is, for example, a partially reflecting mirror, and allows first optical axis 128 to be aligned along the line of sight axis using mire 58 (FIGS. 1 and 3) and telescopic eyepiece 57 in a manner analogous to that outlined in the discussion of the preferred embodiment, above.

Reference detector 124 produces electrical signals at reference leads 129 that are proportional to the deviation of the centroid of the reflection of the reference spot from the center of reference detector surface 126. The signals produced at the reference leads 129 are synchronously detected by, for example, lock-in amplifiers incorporated in error signal electronics 130. Deviations of the image of the reference spot from the center of reference detector 124 are sensed by error signal electronics 130; error signal electronics 130 produces error signals according to the direction of deviation along each of two orthogonal directions on the surface 126 of reference detector 124.

The error signals produced by error signal electronics 130 are used to control an aperture controller 136 to reposition aperture plate 104 with, for example, a servomechanism. By repositioning aperture 102 along one or both of two orthogonal directions perpendicular to the light propagation direction, the locations of both the reference spot and the selected area will be repositioned to generally correct for an eye movement, as will be apparent to one skilled in the art.

In alternate embodiments of the invention, reference and sampling beams could be formed alternately rather than simultaneously. For example, first beam splitter 110 could be replaced with a rapidly oscillating reflecting surface or transparent element such as a rotating silvered sector disk.

In summary, it can be seen that the present invention provides a detailed description of the surface of the eye, and is applicable to topographic characterization of both the corneal and scleral regions. The invention also renders the topographic information in a form which is readily analyzed with a computer and accessible to the ophthalmic practitioner.

While the above is a complete description of the preferred embodiments of the invention, other arrangements and equivalents are possible and may be employed without departing from the true spirit and scope of the invention. For example, if it is not desired that the aperture plate 104 be adjustable to reposition the reference and sample beams in response to eye movements, the reference beam could be produced with a second light source. Also, if deflector 16 were rapidly oscillated to sweep incident light beam 7 across a chosen reference spot repeatedly, and reference detector 124 were monitored synchronously with the reference spot crossing, the reference optical beam could be eliminated while retaining eye movement-correction capability. Further, the triangulation of selected area 8 could be accomplished with second and third optical branches 10 and 10′ without otherwise knowing the position or direction of incident light beam 7. In addition, other arrangements of the optics described could be devised. Therefore, the above description and illustrations should not be construed as limiting the scope of the invention which is delineated by the appended claims.

What is claimed is:

1. An apparatus for determining the topography of a surface of an eye from fluorescence emissions of a fluorescent substance applied to the surface of the eye, the apparatus comprising:
   a light source, emissive of light having a wavelength capable of exciting fluorescence emissions from the fluorescent substance;
   direction means for directing light emitted by the light source onto a selected area of the surface of the eye;
   deflection means for varying the position of the selected area;
   photoelectric detection means for selectively sensing fluorescence emissions from the fluorescent substance in the selected area and for measuring therefrom the position of the selected area; and
   means for determining the topography of at least a portion of the surface of the eye using the measured position of the selected area.

2. An apparatus according to claim 1 wherein:
   the direction means comprises first and second focusing means and means for defining an aperture;
   the first focusing means collects a portion of the light emitted by the light source and directs the collected light through the aperture to the second focusing means; and
   the second focusing means directs the collected light onto the selected area.

3. An apparatus according to claim 1 wherein:
   the deflection means includes an optical cube drivably rotatable about a first rotation axis othogonal to the direction of the collected light.

4. An apparatus according to claim 3 wherein the deflection means further includes means for measuring the extent of rotation of the optical cube.

5. An apparatus according to claim 3 wherein the optical cube is rotatable about an axis substantially orthogonal to each of the first rotation axis and the direction of the collected light.

6. An apparatus according to claim 1 further comprising:
   a position sensitive detector;
   lensing means; and
   partial reflection means disposed between the eye and the deflection means; wherein:
   a portion of the collected light is reflected onto the lens means; and
   the lens means directs the portion of the collected light onto the position sensitive detector for measuring the direction of the collected light.

7. An apparatus according to claim 1 wherein the detection means comprises:
   a photoelectric transducer sensitive to the position of an illuminated area on a surface of the photoelectric transducer; and
   imaging means for producing the illuminated area on the photoelectric transducer surface, the position of the illuminated area being dependent on the position of the selected area of the surface of the eye.

8. An apparatus according to claim 7 wherein the photoelectric transducer is operable to produce electrical signals corresponding to the displacement of the illuminated area along each of two substantially orthogonal directions in a plane defined by the surface of the photoelectric transducer.

9. An apparatus according to claim 8 wherein the detection means includes means for converting each electrical signal produced by the photoelectric transducer into a digitally encoded electronic voltage.

10. An apparatus according to claim 9 wherein the detection means includes a computer for electronically storing the digitally encoded electronic voltages and computing the topography of the surface of the eye therefrom.

11. An apparatus according to claim 1 wherein:
    the direction means includes means for selectively transmitting to the eye the collected light having a wavelength shorter than a portion of the light of which the fluorescent substance is emissive; and
    the detection means includes means for selectively detecting light having a wavelength different from that of the selectively transmitted light.

12. An apparatus according to claim 1 further comprising:
means for varying the intensity of the light emitted by the light source at a selected frequency; and wherein:
the detection means includes means for selectively measuring light having an intensity varying at a selected phase and the selected frequency.

13. An apparatus according to claim 1 wherein the light source is selected from the group consisting of light emitting diodes, solid state lasers, gas lasers, continuous wave lasers, and pulsed lasers.

14. An apparatus according to claim 1 wherein the light source comprises a stroboscopically operable gas-filled discharge lamp.

15. An apparatus according to claim 1 wherein the light source includes:
mechanical light chopping means for periodically varying the intensity of the light emitted from the light source by periodically interposing a light barrier between the light source and the eye.

16. An apparatus according to claim 1 further comprising:
a target mire disposed between the deflection means and the eye, defining an aperture for transmission of the collected light to the eye, and including a luminous target pattern on a surface of the taget mire adjacent the eye; and
means for observing a reflection of the target pattern from the eye, thereby guiding the proper orientation of the light source, the direction means, and the deflection means with respect to the surface of the eye; and
wherein the direction means includes a partial reflector for directing the collected light to the selected area and directing the reflection of the target pattern from the eye to the observing means.

17. An apparatus according to claim 1 adapted such that the fluorescent substance comprises sodium fluorescein.

18. An apparatus according to claim 1 further comprising:
a second light source;
means for varying the intensity of the light emitted by the second light source at a second selected frequency;
a partial reflector disposed between the eye and the deflection means; and
second means for directing light from the second light source towards the partial reflector such that a reference spot on the surface of the eye is illuminated by the second light source; and wherein
at least one of the second means and the second light source is adapted to selectively transmit light having a wavelength different from that of the light of which the fluorescent substance is emissive to the second selected area; and
the second selected area serves as a reference area for compensating for movements of the eye relative to the apparatus.

19. An apparatus according to claim 18 further comprising:
partial reflective means disposed between the direction means and the deflection means for diverting a portion of the collected light; and
wherein the second light source comprises the diverted portion of the collected light.

20. An apparatus for determining the topography of a surface of an eye from fluorescence emissions of a fluorescent substance introduced onto the surface of the eye, the apparatus comprising:
a first optical branch for producing an incident light beam including wavelengths capable of inducing fluorescence emissions from the fluorescent substance, the first optical branch including
a light source,
direction means for directing light from the light source onto a selected area of the surface of the eye, and
deflection means for varying the position of the selected area; and
a second optical branch for measuring the position of the selected area on the surface of the eye, the second optical branch including
imaging means for selecting fluorescence emissions from the fluorescent substance in the selected area and projecting an image of the fluorescence emissions so selected,
photoelectric detection means for determining the position of the image projected by the imaging means, and
means for determining the topography of at least a portion of the surface of the eye employing the position of the projected image.

21. An apparatus according to claim 20 wherein:
the direction means comprises first and second focusing means, and means for defining an aperture;
the first focusing means collects a portion of the light emitted by the light source and directs the collected light through the aperture onto the second focusing means; and
the second focusing means directs the collected light onto the selected area.

22. An apparatus according to claim 20 wherein the deflection means includes means for varying the selected area substantially in a first plane that intersects the surface of the eye.

23. An apparatus according to claim 22 wherein the second optical branch is substantially oriented in a second plane substantially orthogonal to the first plane, whereby a profile of the surface of the eye may be measured by the detection means.

24. An apparatus according to claim 22 wherein the second optical branch is oriented in a third plane substantially parallel to the first plane, whereby the elevation of the selected area may be determined by triangulation.

25. An apparatus according to claim 22 wherein varying means includes an optical cube.

26. An apparatus according to claim 20 wherein:
the first optical branch includes means for selectively transmitting that portion of the incident light beam having a wavelength shorter than the light of which the fluorescent substance is emissive; and
the second optical branch includes means for selectively transmitting to the detection means light having a wavelength different than the light selectively transmitted by the first optical branch.

27. An apparatus according to claim 20 wherein the detection means includes means for producing electrical signals dependent on the displacement of the image along each of to substantially orthogonal directions.

28. An apparatus according to claim 27 wherein the intensity of the incident light beam may be modulated at a selected frequency; and including means for measuring each electrical signal synchronously with the selected frequency to produce a first signal corresponding to the amplitude of the component of each electrical signal varying at the selected frequency.

29. An apparatus according to claim 28 further comprising means for converting each first signal into a digitally-encoded position signal.

30. An apparatus according to claim 29 further comprising:
an incident beam locator having a position sensitive detector, lensing means, and a partial reflector disposed between the eye and the deflection means; and
wherein a portion of the incident light beam is directed onto the lensing means and directed by the lensing means onto the position sensitive detector for measuring the direction of the incident light beam; and
wherein the position sensitive detector is operable to produce second signals in response to the position of the portion of the incident light beam.

31. An apparatus according to claim 30 further comprising:
electronic detection means sensitive to the selected frequency for analyzing the second signals and generating location signals therefrom; and
means for converting each location signal into a digitally-encoded location signal.

32. An apparatus according to claim 31 further comprising a computer for storing each digitally-encoded position signal and each digitally encoded location signal and calculating the topography of the eye therefrom.

33. An apparatus for determining, from fluorescence emissions of a fluorescent substance, the topography of the surface of an eye having a coating including the fluorescent substance, the apparatus comprising:
a first optical branch for producing a sampling light beam and a reference light beam, the first optical branch including
a light source adapted to emit light capable of exciting fluorescence emissions from the fluorescent substance,
first direction means for directing light in the sampling light beam from the light source onto a selected area of the surface of the eye,
second direction means for directing light in the reference light beam from the light source onto a reference spot on the surface of the eye, and
deflection means for varying the position of the selected area relative to the position of the reference spot; and
a second optical branch for measuring the position of the selected area and the position of the reference spot on the surface of the eye, the second optical branch including:
imaging means for selectively projecting an image of the fluorescent light emitted by the fluorescent substance in the selected area and in the reference spot;
photoelectric detection means for locating the image to determine both the position of the reference spot and the position of the selected area on the surface of the eye; and
means for determining the topography of at least a portion of the surface of the eye using the positions of the reference spot and the selected area.

34. The apparatus of claim 33 wherein the detection means comprises a photosensitive transducer productive of electrical responses from light incident onto a surface of the detection means, the electrical responses corresponding to the position of the image along each of two substantially orthogonal directions.

35. The apparatus of claim 34 wherein the first optical branch includes:
first modulation means for varying the intensity of the reference light beam at a first modulation frequency; and
second modulation means for varying the intensity of the sampling light beam at a second modulation frequency.

36. The apparatus of claim 35 wherein the second optical branch includes means for selectively measuring the electrical responses of the photosensitive transducer at each of the first and second modulation frequencies.

37. The apparatus of claim 33 further comprising:
a position sensitive detector;
lensing means; and
partial reflection means disposed between the eye and the first optical branch; wherein:
a portion of the sampling light beam is directed onto the lensing means; and
the lensing means directs the portion of the sampling light beam onto the position sensitive detector for measuring the direction of the sampling light beam.

38. The apparatus of claim 33 wherein the first optical branch includes reference means for measuring the position of a reflection of the reference beam from the eye.

39. The apparatus of claim 38 wherein the reference means comprises:
a reference detector responsive to the position of an illuminated area on a surface of the reference detector and productive of reference signals indicative of the position of the illuminated area along each of two substantially orthogonal directions;
a reference beam splitter for directing a portion of the reflection of the reference beam onto the surface of the reference detector; and
a reference lens for making the surface of the eye and the surface of the reference detector approximately conjugate.

40. The apparatus of claim 39 wherein the reference detector further comprises:
measurement means for selectively measuring the reference signals produced in response to the reflection of the reference beam from the eye, and for producing reference position signals therefrom.

41. The apparatus of claim 40 including means for varying the intensity of the reference beam at a first modulation frequency, wherein the measurement means comprises a means for measuring the reference signals synchronously with the first modulation frequency.

42. The apparatus of claim 40 wherein the first optical branch includes correction means for varying the position of the reference spot in response to the magnitude of the reference position signals.

43. The apparatus of claim 39 further comprising:
a target mire disposed between the first optical branch and the eye, the target mire having a luminous target pattern on a surface of the target mire adjacent the eye and an aperture for transmitting the reference light beam, the sampling light beam, the reflection of the reference beam, and a reflection of the target pattern from the eye; and means for observing the reflection of the target pattern from the eye through the reference lens and the reference beam splitter.

44. A method for determining the topography of a surface of an eye comprising the steps of:
applying a material including a fluorescent substance to the surface of the eye;
directing a sampling beam of light to the surface of the eye, thereby defining a selected area of the surface of the eye;
imaging the selected area from a direction different from the direction of the sampling beam;
selectively photoelectrically detecting the imaged fluorescence emitted in the selected area; and
determining the topography of at least a portion of the surface of the eye from the imaged fluorescence.

45. The method of claim 44 further comprising the step of triangulating the elevation of the surface of the eye in the selected area from the position and direction of the sampling beam and the position and direction of the image of the selected area.

46. The method of claim 44 further comprising the step of profiling a segment of a meridian of the surface of the eye from the position and direction of the image of the selected area.

47. The method of claim 44 further comprising the step of:
aligning the sampling beam approximately along the line of sight axis of the eye.

48. The method of claim 44 further comprising the steps of:
varying the position of the sampling beam to different portions of the surface of the eye; and
accumulating the position of each thereby defined selected area.

49. The method of claim 44 further comprising the steps of:
directing a reference beam to the surface of the eye, thereby defining a reference spot;
detecting the emissions of the fluorescent substance in the reference spot; and
measuring the position of the reference spot from a perspective different from the direction of the reference beam.

50. The method of claim 49 further comprising the steps of:
detecting the position of a reflection of the reference beam from the eye; and
varying the direction of the reference beam and the sampling beam in response to changes in the position of the reflection.

51. An apparatus according to claim 20 wherein the light source is a laser.

52. An apparatus according to claim 20 wherein the deflection means includes a mirror drivably rotatable about a first rotation axis.

53. An apparatus according to claim 52 wherein the mirror is rotatable about a second rotation axis different from the first rotation axis.

54. An apparatus according to claim 52 wherein the deflection means further includes a second mirror rotatable about a second rotation axis.

55. An apparatus according to claim 20 wherein:
the light source is emissive of substantially monochromatic light having a wavelength shorter than a portion of the light of which the fluorescent substance is emissive; and
the second optical branch includes an optical filter for selectively transmitting to the detection means light having a wavelength longer than the monochromatic light.

56. An apparatus according to claim 20 further comprising:
an incident beam locator having a position sensitive detector, lensing means, and a partial reflector disposed between the eye and the deflection means; and
wherein a portion of the incident light beam is directed onto the lensing means and directed by the lensing means onto the position sensitive detector for measuring the direction of the incident light beam; and
wherein the position sensitive detector is operable to produce output signals in response to the position of the portion of the incident light beam.

57. An apparatus according to claim 56 further comprising:
means for varying the intensity of the incident light beam at a selected frequency;
electronic detection means sensitive to the selected frequency for analyzing the output signals and generating location signals therefrom; and
means for converting each location signal into a digitally-encoded location signal.

58. An apparatus according to claim 1 wherein the detection means includes a detector array.

59. An apparatus according to claim 20 wherein the imaging means includes a detector array.

60. An apparatus according to claim 33 wherein the imaging means includes a detector array.

* * * * *